(12) United States Patent
Rowe et al.

(10) Patent No.: US 9,375,210 B2
(45) Date of Patent: Jun. 28, 2016

(54) APICAL PUNCTURE ACCESS AND CLOSURE SYSTEM

(71) Applicant: Edwards Lifesciences Corporation, Irvine, CA (US)

(72) Inventors: Stanton J. Rowe, Newport Coast, CA (US); Ming H. Wu, Tustin, CA (US); Ralph Schneider, Trabuco Canyon, CA (US); Philip P. Corso, Jr., Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 14/735,034

(22) Filed: Jun. 9, 2015

(65) Prior Publication Data

US 2015/0272559 A1  Oct. 1, 2015

Related U.S. Application Data

(62) Division of application No. 13/434,633, filed on Mar. 29, 2012, now Pat. No. 9,055,937.

(60) Provisional application No. 61/470,930, filed on Apr. 1, 2011.

(51) Int. Cl.

| A61B 1/00 | (2006.01) |
|---|---|
| A61B 17/00 | (2006.01) |
| A61B 17/02 | (2006.01) |
| A61B 17/34 | (2006.01) |

(52) U.S. Cl.
CPC ....... *A61B 17/0057* (2013.01); *A61B 17/00234* (2013.01); *A61B 17/02* (2013.01); *A61B 17/0293* (2013.01); *A61B 17/3478* (2013.01); *A61B 2017/00243* (2013.01); *A61B 2017/00247* (2013.01); *A61B 2017/00579* (2013.01); *A61B 2017/00592* (2013.01); *A61B 2017/00597* (2013.01); *A61B 2017/00601* (2013.01); *A61B 2017/00606* (2013.01); *A61B 2017/00623* (2013.01); *A61B 2017/00628* (2013.01); *A61B 2017/00637* (2013.01); *A61B 2017/00668* (2013.01); *A61B 2017/00867* (2013.01); *A61B 2017/00991* (2013.01); *A61B 2017/0237* (2013.01); *A61B 2017/3425* (2013.01)

(58) Field of Classification Search
CPC .......... A61B 1/00; A61B 17/02; A61B 17/00; A61B 17/34; A61B 17/0293
See application file for complete search history.

(56) References Cited

U.S. PATENT DOCUMENTS

| 4,994,071 A * | 2/1991 | MacGregor ................... 606/194 |
|---|---|---|
| 2005/0177224 A1* | 8/2005 | Fogarty et al. ............... 623/1.35 |

* cited by examiner

*Primary Examiner* — Victor Nguyen
(74) *Attorney, Agent, or Firm* — Richard B. Cates; AnnMarie Kaiser

(57) ABSTRACT

A device, system, and method for providing access to, and sealing of, a body organ includes an implant device. An implant device has a main body having an internal access lumen, with a plurality of prongs extending from a distal end of the main body. The main body can include two lumens, one slidable within the other, to form a single continuous lumen with an adjustable length. The main body has an expanded configuration with an expanded diameter, and an unexpanded configuration with an unexpanded diameter. The prongs have a generally straight configuration where they extend distally of the distal end of the main body, and a bent configuration where the prongs bend around so that their tips extend proximally of the distal end of the main body. The device may include a hemostatic barrier to prevent fluid leakage therethrough when the main body is in the unexpanded configuration.

12 Claims, 14 Drawing Sheets

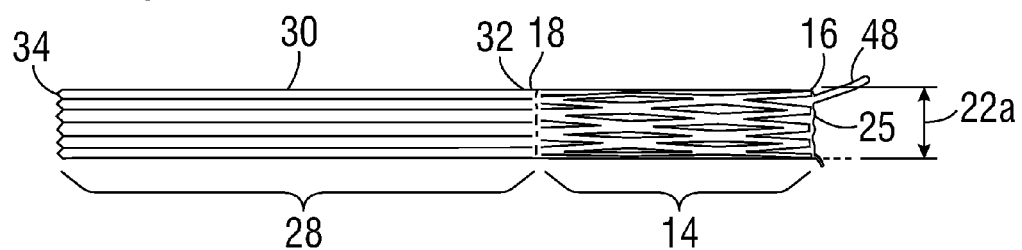
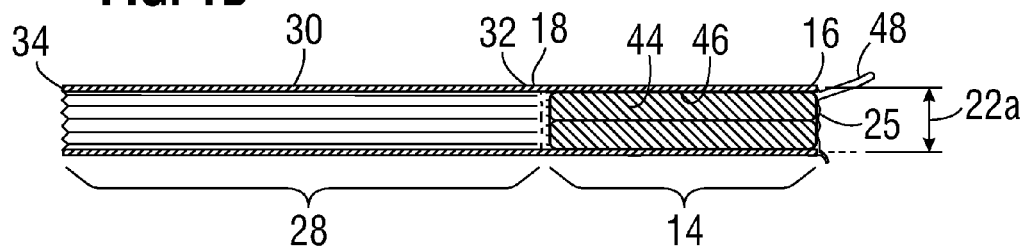
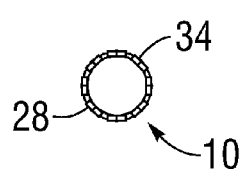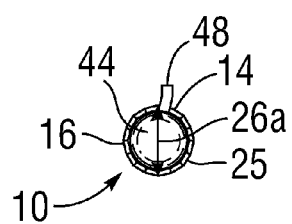

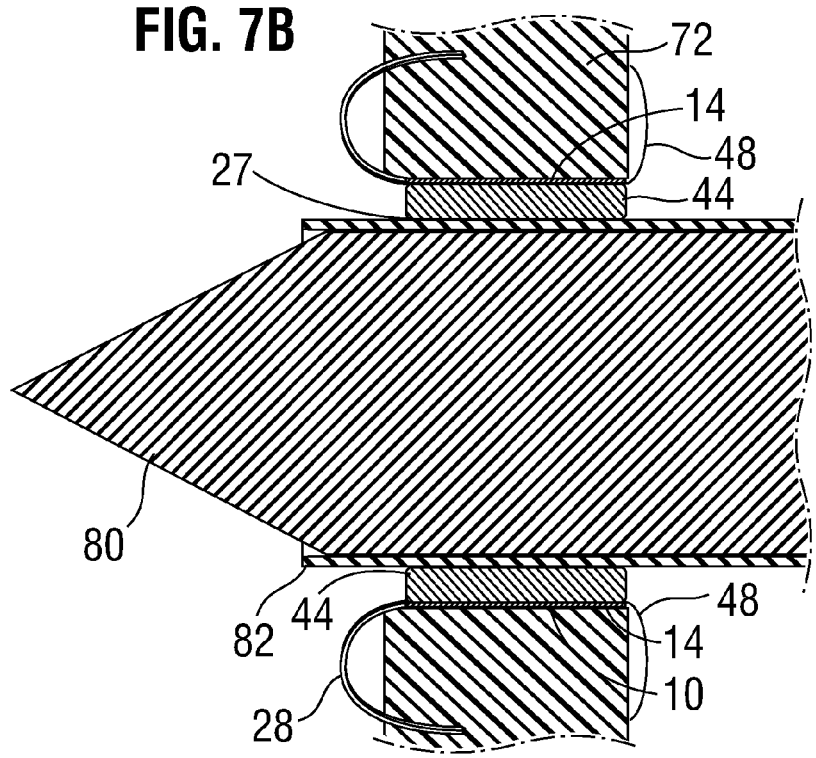
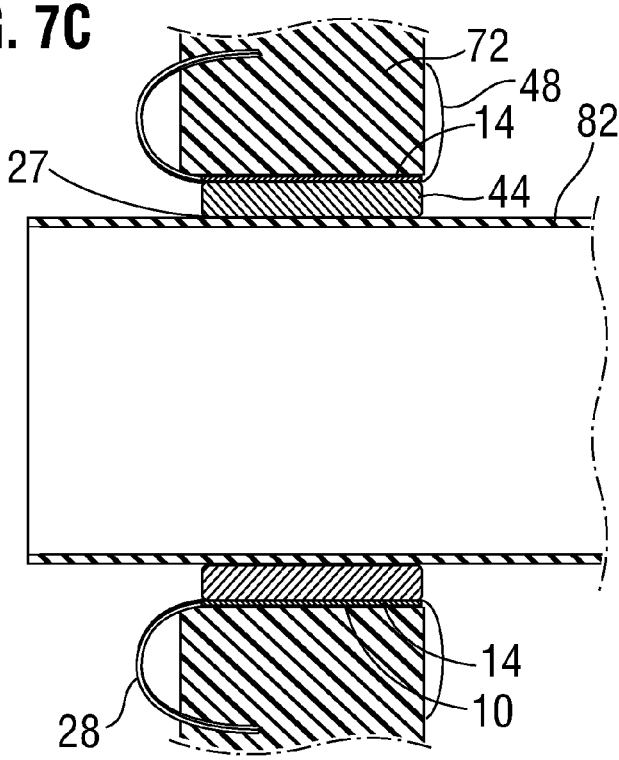

APICAL PUNCTURE ACCESS AND CLOSURE SYSTEM

CROSS REFERENCE TO RELATED APPLICATIONS

The application is a divisional of U.S. patent application Ser. No. 13/434,633, filed on Mar. 29, 2012, which claims the benefit of U.S. application Ser. No. 61/470,930, filed Apr. 1, 2011, the entire disclosures of which are incorporated by reference herein.

FIELD OF THE INVENTION

The present invention relates to methods and systems for cinching a tissue puncture around an implement and closing the puncture after removal of the implement, in particular for punctures in heart tissue.

BACKGROUND OF THE INVENTION

The heart is a hollow muscular organ of a somewhat conical form; it lies between the lungs in the middle mediastinum and is enclosed in the pericardium. The heart rests obliquely in the chest behind the body of the sternum and adjoining parts of the rib cartilages, and typically projects farther into the left than into the right half of the thoracic cavity so that about one-third is situated on the right and two-thirds on the left of the median plane. The heart is subdivided by septa into right and left halves, and a constriction subdivides each half of the organ into two cavities, the upper cavity being called the atrium, the lower the ventricle. The heart therefore consists of four chambers; the right and left atria, and right and left ventricles, with one-way flow valves between respective atria and ventricles and at the outlet from the ventricles.

Heart valve replacement may be indicated when there is a narrowing of a native heart valve, commonly referred to as stenosis, or when the native valve leaks or regurgitates, such as when the leaflets are calcified. When replacing the valve, the native valve may be excised and replaced with either a biologic or a mechanical valve.

Conventional heart valve surgery is an open-heart procedure conducted under general anesthesia, and is a highly invasive operation. The first 2-3 days following surgery are spent in an intensive care unit where heart functions can be closely monitored. The average hospital stay is between 1 to 2 weeks, with several more weeks to months required for complete recovery.

In recent years, advancements in minimally-invasive surgery and interventional cardiology have encouraged some investigators to pursue percutaneous replacement of the aortic heart valve. Percutaneous Valve Technologies ("PVT"), formerly of Fort Lee, N.J. and now part of Edwards Lifesciences of Irvine, Calif., has developed a plastically- or balloon-expandable stent integrated with a bioprosthetic valve. The stent/valve device, now called the Edwards Sapien™ Heart Valve, is deployed across the native diseased valve to permanently hold the valve open, thereby alleviating a need to excise the native valve. The Edwards Sapien™ Heart Valve is designed for delivery with the RetroFlex™ delivery system in a cardiac catheterization laboratory under local anesthesia using fluoroscopic guidance, thereby avoiding general anesthesia and open-heart surgery.

Some researchers propose implanting prosthetic heart valves at the aortic annulus using a direct-access transapical (through the left ventricular apex) approach (e.g., U.S. Patent Publication No. 2006-0074484). The left ventricular apex LVA is directed downward, forward, and to the left (from the perspective of the patient). The apex typically lies behind the fifth left intercostal space (or between the fourth and fifth), 8 to 9 cm from the mid-sternal line, and about 4 cm below and 2 mm to the medial side of the left mammary papilla. Access to the left ventricle may therefore be attained through an intercostal incision positioned over the fifth left intercostal space. Such an approach is often termed a "mini-thoracotomy," and lends itself to surgical operations on the heart carried out using one or more short tubes or "ports"—thus, the operations are often referred to as "port-access" procedures.

Dehdashtian in U.S. Patent Publication No. 2007-0112422 discloses a port-access delivery system for transapical delivery of a prosthetic heart valve including a balloon catheter having a steering mechanism thereon that passes through an access device such as an introducer. The surgeon forms a puncture in the apex with a needle, advances a guidewire, then a dilator, and finally the introducer. Purse string sutures are pre-installed around the puncture to seal against blood leakage around the various devices and provide a closure after the procedure. During the procedure the doctor/assistant is able to apply tension to the purse-string-suture, which prevents inadvertent blood loss. After the deployment of the heart valve, the purse sting-suture is then used to permanently close the opening of the heart by drawing concentric tension on the suture ends, and tying a secure knot. The aforementioned Edwards Sapien™ Heart Valve may be inserted transapically with the Ascendra™ delivery system, much like the system disclosed in Dehdashtian.

Purse string sutures are often affixed to the heart, major arteries, and/or major veins to permit secure placement of tubes for cardiopulmonary bypass (CPB), for instance. Specifically, purse string sutures are used to seal the tissue around a cannula placed within the cardiac tissue. A purse string suture usually consists of a synthetic filament placed in a circular pattern, which is secured by taking four to five bites of tissue placed at uniform intervals around a tube, for example, from positions (with respect to a 12-hour clock face) at 1:00 to 2:00, 4:00 to 5:00, 7:00 to 8:00, and 10:00 to 11:00. Two concentric sutures usually are employed in the event that one suture breaks, and to help minimize bleeding around the surgically inserted tube. If blood pressure is not excessively high, a single purse string suture can be employed. When the tube is removed at the end of the procedure, the two ends of each suture filament are tied together to produce a water-tight seal. Examples of improved devices and methods for applying purse string sutures are disclosed in U.S. Utility patent application Ser. No. 12/844,139, filed Jul. 27, 2010 and entitled "Surgical Puncture Cinch and Closure System," in U.S. Provisional Application No. 61/418,188, filed Nov. 30, 2010 and entitled "Surgical Stabilizer and Closure System," in U.S. Provisional Application No. 61/252,114, filed Oct. 15, 2009 and entitled "Surgical Puncture Cinch and Closure System," and in U.S. Provisional Application No. 61/229,190, filed Jul. 28, 2009 and entitled "Surgical Puncture Cinch and Closure System," the entire contents of each of which are hereby incorporated herein by reference.

What has been needed is an improved method and device for closing an apical puncture which provides access to the heart interior for a medical procedure and also seals the puncture once the medical procedure is completed. The current invention meets those needs.

SUMMARY OF THE INVENTION

More specifically, the present application describes several devices through which a direct-access port (or other access instruments) may be introduced, with the devices sealing against blood loss around the direct-access port (or other access instruments) and also closing the puncture after removal of the port. More broadly, the devices described herein may be utilized in the context of various cardiac and other surgeries that benefit from hemostatic sealing with access to internal spaces while permitting closure of a puncture wound.

The present invention may be used for delivery of a prosthetic (i.e., replacement) heart valve to a native valve site without an open chest procedure, with a combined access/sealing device applied to a puncture in the heart wall to provide access through which devices may be introduced into the heart and/or to seal the puncture at the conclusion of the procedure.

A device according to an embodiment of the invention has a generally elongated and radially-expandable main body with a distal end and a proximal end and an internal lumen. In some embodiments, the main body comprises a distal portion having a distal end and a distal lumen and a proximal portion having a proximal end and a proximal lumen, the distal lumen being sized to receive the proximal lumen, thereby creating a continuous internal lumen through the main body. The main body can be radially expanded and/or radially retracted between an unexpanded configuration having an unexpanded outer diameter and an expanded configuration having an expanded outer diameter. A plurality of prongs extend from the distal end of the main body, each of the prongs comprising a proximal end secured to the distal end of the main body, and a distal end which may include a sharp/pointed distal tip. Each of the prongs may have a straight configuration where the prong is generally straight and extends generally distally from the main body distal end such that the distal end of the prong is positioned distally of the main body. Each of the prongs may have a bent configuration where the prong is generally curved such that the distal end of the prong is positioned radially outward from the main body. The distal end of the prong in the bent configuration may also be positioned proximally of the distal end of the main body.

The device may have a delivery configuration, an access configuration, and a closed configuration. In the delivery configuration the main body may be in the unexpanded configuration with the prongs in the straight configuration. In the access configuration the main body may be in the expanded configuration with the prongs in the curved configuration. In the closed configuration the main body may be in the unexpanded configuration with the prongs in the curved configuration.

All or part of the structure of the device, e.g., the prongs and/or main body, may comprise a memory material such as Nitinol. In one embodiment, the main body comprises a memory material having a relaxed state. The main body may be biased, when in the relaxed state, toward the unexpanded or closed configuration. The prongs may comprise a memory material having a relaxed state, and the prongs may be biased, when in the relaxed state, toward the curved configuration.

The prongs and main body may be formed as a single unitary structure, e.g., may be formed from a single tube of material with cutouts formed therein to define the main body and/or prongs.

The device main body may have an unexpanded external diameter when the main body is in the unexpanded configuration, with the main body having an expanded external diameter when the main body is in the expanded configuration, with the unexpanded external diameter being smaller than the expanded external diameter. The expanded external diameter may be in the range of 10 to 20 millimeters, such that catheters and/or other instruments may be advanced therethrough to access the inner portion of the heart or other organ. The unexpanded internal diameter may be in the range of 3 to 5 millimeters. The opening through the device (through which catheters and/or other medical devices may be introduced) can vary from 0 (i.e., closed/sealed) when in the unexpanded configuration to 6 or 8 millimeters or more when in the expanded configuration.

The main body may have a length, or can be adjusted to have a length, on the order of, or substantially equal to, the thickness of the heart (or other organ) wall at the position wherein the device is to be deployed. For example, if the device is to be deployed in the heart apex, the device will have a length about the same as the thickness of the apical heart wall. For a device to be deployed through the heart apex, the length of the device main body may be in the range of about 5 to 20 millimeters, or in a smaller range such as about 6 to 15 millimeters.

The prongs have a length sufficient to extend radially from the main body while simultaneously engaging into the organ wall tissue to secure the device therein. The prongs may be configured so that they will extend into the organ wall tissue but without extending all the way through the heart wall tissue. For example, the prong may have a length of about 5 mm to 25 millimeters, or in a smaller range such as about 6 to 22 millimeters.

A device according to an embodiment of the invention may include a hemostatic bather positioned within the main body and configured to further narrow and/or seal the inner lumen to prevent fluid leakage through the inner lumen when the main body is in the unexpanded configuration. The hemostatic bather may have sufficient bulk to block most or all of the length and/or diameter of the inner lumen when the device is in the unexpanded configuration. The hemostatic barrier may comprise a sealing fabric, which may cover the internal walls of the lumen of the main body. The main body in its unexpanded configuration may exert a radially inward force against the sealing fabric to improve the seal.

A portion of the device, such as a portion of the sealing fabric, may extend proximally past the proximal end of the main body, e.g., by a distance of 5 mm or more, to facilitate securing of the sealing fabric or other portion to tissue of the patient. This could be useful to enhance securement of the device to the organ wall.

A method according to an embodiment of the invention for providing access through an organ wall may include any or all of the following: providing a hemostatic sealing device comprising a main body having a distal portion with a distal lumen and a proximal portion with a proximal lumen, where the distal lumen is sized to receive the proximal lumen so as to create a continuous lumen through the main body, the sealing device further comprising a plurality of prongs extending from a distal end of the main body, wherein the main body lumen has a first diameter, and the plurality of prongs are radially retracted with respect to the main body; forming a hole in an organ wall of an organ; advancing the hemostatic sealing device into the hole in the organ wall until the distal portion of the main body is advanced at least partially into an interior space of the organ; adjusting the overall length of the device by sliding the proximal lumen into or out of the distal lumen such that the distal portion of the main body is within the interior space of the organ and the proximal portion of the main body is positioned outside the organ wall; extending the prongs so that the prong tips are extended radially away from the main body; and/or securing the hemostatic sealing device in the organ wall by retracting the main body at least partially out of the interior space of the organ and embedding the prong tips into the organ wall from an interior surface thereof. In some embodiments, the proximal portion of the main body is positioned at an incision site in the patient's skin Further steps of a method according to an embodiment of the invention may include, after securing the hemostatic sealing device to the organ wall, radially expanding the main body lumen from the first diameter to a second diameter, wherein the second diameter is larger than the first diameter; and advancing an access sheath into the sealing device. Radially expanding the main body lumen may comprise advancing a dilator into the main body lumen. The method may comprise the further step of, after advancing the access sheath into the sealing device, retracting the dilator from the sealing device while leaving the access sheath positioned within the sealing device. The method may comprise the further steps of: advancing a treatment catheter through the main body lumen and into an interior of the organ; performing a treatment via the treatment catheter within the interior of the organ; and/or withdrawing the treatment catheter from the interior of the organ via the main body lumen. The treatment catheter may comprise a device delivery catheter, and performing the treatment may comprise deploying the device within the interior of the organ.

The organ being accessed may be a heart, and forming the hole in the organ wall may comprise forming a hole in the apex of the heart, and securing the hemostatic device in the organ wall may comprise securing the hemostatic device in the apex of the heart. The method may comprise providing a delivery catheter with a prosthetic heart valve on a distal portion of the delivery catheter; advancing the distal portion of the delivery catheter, with the prosthetic heart valve thereon, through the access sheath and through the main body lumen of the hemostatic device and thus through the apex and into the interior of the heart; positioning the prosthetic heart valve within a native heart valve annulus; deploying the prosthetic heart valve within the native heart valve annulus; withdrawing the delivery catheter from the interior of the heart and out of the access sheath and main body lumen of the hemostatic device, wherein the prosthetic heart valve remains deployed within the native heart valve annulus; withdrawing the access sheath from the main body lumen; and/or radially retracting the main body lumen from the second diameter to a smaller diameter. The access sheath may be generally resistant to radial compressive forces, with the hemostatic device biased toward a smaller diameter than the second diameter, and withdrawing the access sheath from the main body lumen may permit the main body lumen to radially retract from the second diameter to the smaller diameter.

A system for providing access through an organ wall and for sealing the organ wall according to the invention may comprise an access device as previously disclosed, and an access device delivery catheter comprising a generally elongated catheter body having a distal portion and a proximal portion, wherein the proximal portion comprises a control handle, and wherein the access device is positioned at or on the distal portion. A system may further include a trocar for creating the hole in the organ wall, a dilator for radially expanding the device main body, and/or an access sheath to hold the device in the expanded configuration and/or to provide access therethrough for catheters and other treatment/surgical instruments.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 1A-1D are side, side (in cross-section), distal end, and proximal end views of an example of a device in a delivery configuration according to an embodiment of the current invention;

FIGS. 7A-7D depict side views of a heart wall and device during a procedure being conducted within the heart using a catheter according to an embodiment of the invention;

DETAILED DESCRIPTION OF THE PREFERRED EMBODIMENTS

Figure 2A:
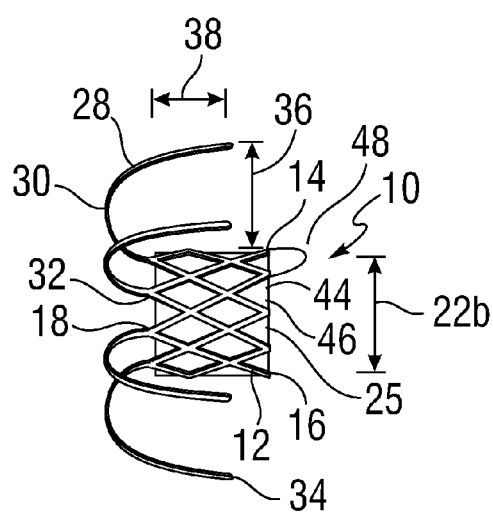
FIGS. 2A-2D are side, side (in cross-section), distal end, and proximal end views of the device of FIGS. 1A-1D, with the device in an expanded configuration according to an embodiment of the invention.
Figure 2B:
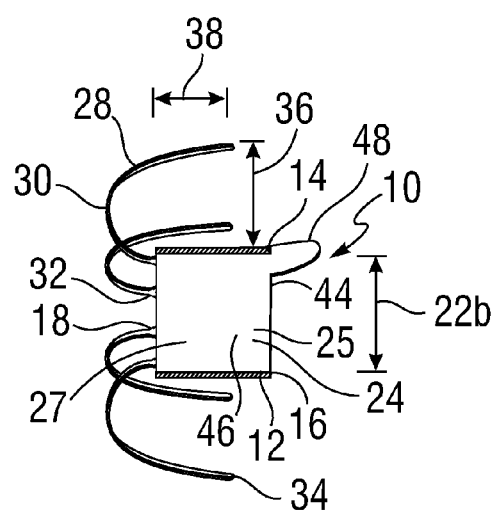
Figure 2C:
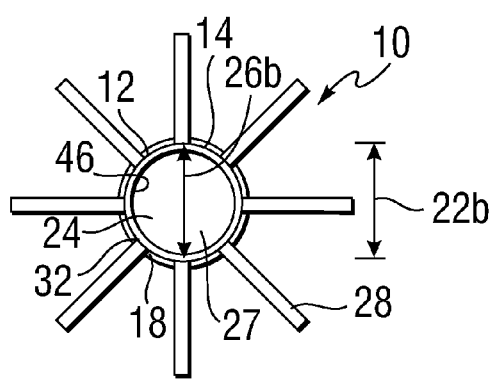
Figure 2D:
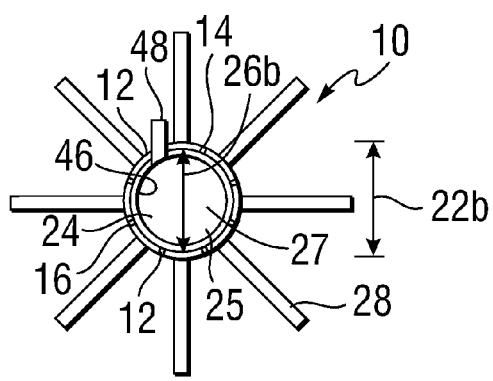
Figure 3A:
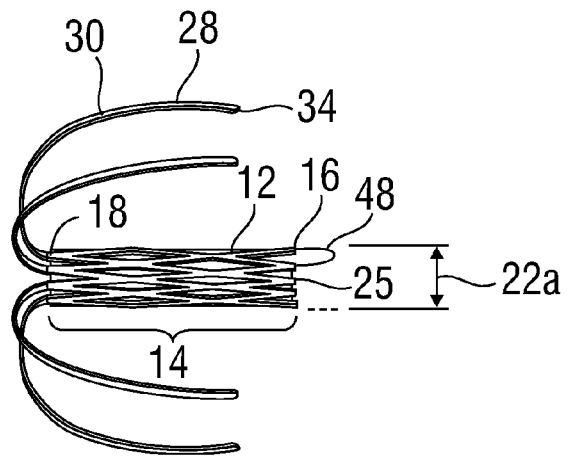
FIGS. 3A-3D are side, side (in cross-section), distal end, and proximal end views of the device of FIGS. 1A-1D, with the device in a closed configuration according to an embodiment of the invention.
Figure 3B:
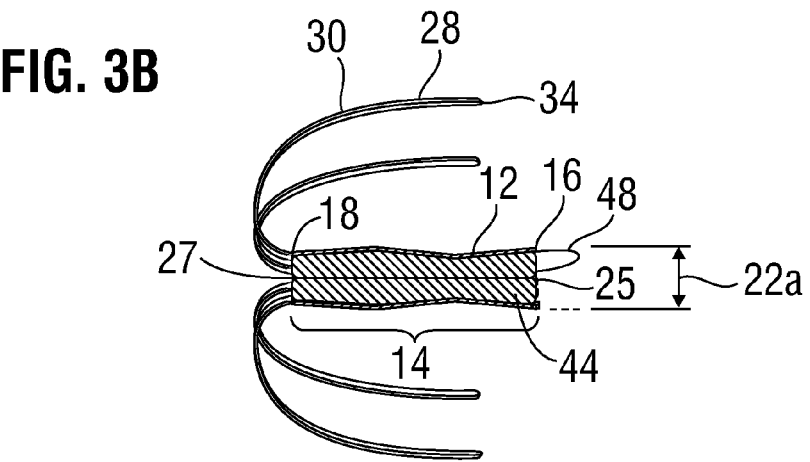
Figure 3C:
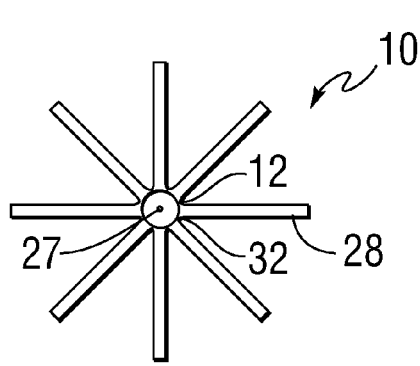
Figure 3D:
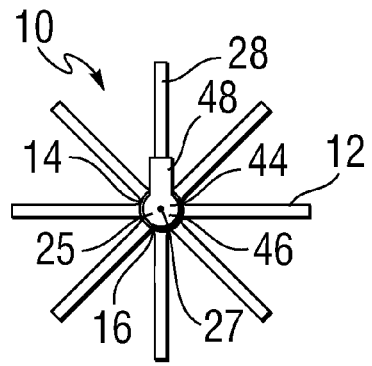
Figure 4:
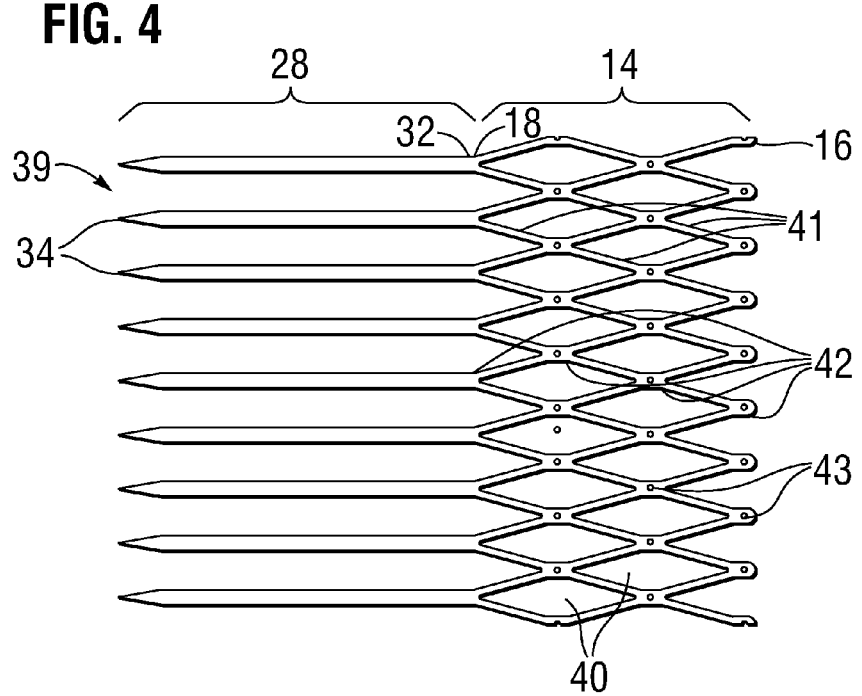
FIG. 4 is a view of a cutting pattern used to create a support stent according to an embodiment of the invention.

FIGS. 1A-1D, 2A-2D, 3A-3D, and 4 depict a hemostatic closure/access device 10 according to an embodiment of the invention. In FIGS. 1A-1D, the device 10 is in a delivery configuration for delivery to a treatment site in a patient. In FIGS. 2A-2D, the device 10 is expanded in an access configuration to provide an access passage to the interior of a target body organ, and in FIGS. 3A-3D the device 10 is in a closed configuration to seal the access passage. FIG. 4 depicts an exemplary cutting pattern used to create the stent-like framed structure 12 (aka support stent) of the device 10.

The device 10 includes a stent-like framed structure 12 having a main body 14 with a proximal end 16 and a distal end 18. The main body 14 in this embodiment is generally cylindrical, having a length 20 and an outside diameter 22a, 22b. An inner lumen 24 extends through the main body 14. The inner lumen 24 has a proximal opening 25, and includes a lumen diameter 26. The main body 14 can be radially expanded and then contracted.

The main body 14 is configured to go from an unexpanded diameter 22a (depicted in FIGS. 1A-1D) to an expanded diameter 22b (depicted in FIGS. 2A-2D), and back to the unexpanded diameter 22a (depicted in FIGS. 3A-3D). During the radial expansion and contraction of the main body 14, the main body inner lumen 24 goes from its unexpanded internal diameter 26a to its expanded internal diameter 26b and back again.

A plurality of prongs 28 extends from the distal end 18 of the main body 14. The prongs 28 have central bodies 30, with proximal ends 32 and distal ends 34. The prongs 28 are secured at their proximal ends 32 to the distal end 18 of the main body 14. The distal ends 34 are preferably sharpened. The prongs 28 are configured to go from a straight configuration, depicted in FIGS. 1A-1D, where the prongs 28 extend distally and in general longitudinal alignment with the main body 14, to a curved configuration, depicted in FIGS. 2A-2D and 3A-3D, where the prong distal ends 34 are positioned proximally and radially outwardly from the distal end 18 of the main body 14.

The stent-like structure 12 may be a single one-piece unitary structure, where the prongs 28 and main body 14 are formed as a single piece. The prongs 28, main body 14, or even the entire stent-like structure 12 may be formed from a memory material, such as Nitinol™. In one embodiment of the invention, the main body 14 in its relaxed configuration assumes its smaller, unexpanded diameter. In an embodiment of the invention, the prongs 28 in their relaxed state assume their curved configuration. In an embodiment of the invention, the main body 14 assumes its unexpanded diameter and the prongs 28 assume their curved state, so that the device 10 in its relaxed state assumes the closed configuration of FIGS. 3A-3D.

In one embodiment, the support structure 12 is cut from a unitary tube of a material such as Nitinol™. The tube will typically be hollow, with a lumen therethrough, with the tube's outer surface forming a solid wall prior to being cut with the desired pattern. An exemplary cutting pattern 39 is depicted in FIG. 4. Note that the pattern 39 is depicted in FIG. 4 in a two-dimensional "rolled-out" fashion, as if the tube had been cut and rolled out into a flat sheet with the pattern thereon. In actual operation, the cutting pattern 39 would be cut into a tube itself, without the tube being formed into a flat section. The cutting pattern 39 defines the prongs 28, which in the particular embodiment depicted include distal ends 34 which are relatively sharp for easier entry into tissue such as the heart wall. The cutting pattern 39 also defines the main body 14, with the proximal ends 32 of the prongs 28 beginning at the distal end 18 of the main body 14. The main body 14 is formed from multiple cut-out openings 40 which define struts 41 connected via joints 42. The joints 42 may include small holes 43 cut therein which may function as stress-relief cutouts and/or as openings through which suture or other components may be advanced (e.g., a suture used to secure a hemostatic seal to the support structure).

Once the selected pattern is cut into the initial tube, the excess material is removed to form the "raw" support structure. The support structure is then subjected to a shape setting process, which may include physically deforming/constraining the raw support structure into the desired final (aka "relaxed") shape. In a preferred embodiment of the invention, the desired final shape is generally a shape such as that depicted in FIGS. 3A-3D, with the prongs 28 curved backwards and the main body 14 in its unexpanded (e.g., closed) configuration. The physical deformation, which may be performed using a mold, mandrel, or similar device, constrains/bends the prongs to the desired curved shape and also constrains/compresses the main body to its desired unexpanded/closed configuration. Once the support structure is in the desired final shape, the support structure is subjected to heat treatment, as is known in the art, in order to set (aka "train") the support structure to retain (and after subsequent deformation to return to) the desired final shape.

The device 10 may include a hemostatic seal 44 positioned within the inner lumen 24. In the particular embodiment depicted, the hemostatic seal 44 comprises a layer of sealing fabric 46 covering the inner lumen 24 of the stent-like structure 12 to form a defined hemostatic barrier. The sealing fabric 46 may be configured to accommodate full expansion of the main body 14 while covering the inner surface of the lumen 24 completely. When the main body 14 is expanded (as depicted in FIGS. 2A-2D), the hemostatic seal 44 is pressed radially outward against the inner sides of the main body such that there is an opening/access passage 27 through the inner lumen 24 through which a catheter or other treatment device may be advanced. The opening/access passage 27 may be shaped and sized to permit a catheter and/or other medical device(s) to be advanced through the opening/access passage 27 while leaving little or no open space around the catheter and/or other medical device(s) through which blood (or other fluids) might otherwise flow out of or into the organ interior.

The opening/access passage 27 formed in an expanded device 10, such as that depicted in FIGS. 2A-2D, may preferably be sized to have about the same shape and size as the cross-section of a catheter/other device being introduced therethrough. For example, where a catheter having a generally circular cross-section and an external diameter of 6 French (6 Fr, which equals 2 millimeters) is advanced into a body organ via the device 10, the opening/access passage 27 (when the device 10 is in an expanded configuration) may be generally circular and have a diameter about the same as the catheter (e.g., about 2 mm, or maybe slightly more). By matching the opening/access passage 27 size and shape to the particular catheter used during a procedure, the catheter can be advanced through the opening/access passage 27 and into the organ while fitting relatively tightly within the opening/access passage 27 in order to prevent fluid flow around the catheter and through the device 10.

The hemostatic seal 44 may be configured to compress against and/or otherwise conform to the exterior surface of the catheter and/or other medical device(s) to provide a tight seal therearound. The main body 14 in its expanded configuration may exert a defined force radially inward against the sealing fabric or other elements of the hemostatic seal 44, with the inward force compressing the sealing fabric and/or otherwise helping the hemostatic seal to seal off and prevent blood (or other fluid(s)) from flowing through any space between the main body 14 and any catheter or other treatment device advanced through the main body 14. The sealing fabric 46 or other portions of the hemostatic seal 44 may extend for most or all of the length of the inner lumen 24, so that when the device 10 is expanded the access opening 27 is formed as a generally elongated access lumen through which the treatment device(s) may be advanced. Such a configuration may provide additional sealing around the catheter(s)/other treatment device(s) positioned within the access opening 27. The inward pressure from the main body (which may cause or result from the main body being biased toward a smaller outer diameter) may help to reduce the main body diameter to a smaller (e.g., unexpanded) diameter and/or also help to close the opening/access passage 27 when the catheter or other medical device(s) are withdrawn from the device 10.

The device 10 may be configured so that the size of the access opening 27 can vary in diameter or other dimension in order to accommodate different medical device(s) of various sizes. For example, the device 10 may be configured to that the size of the access opening 27 can be expanded from 0 millimeters (i.e., closed) to any open diameter (or diameters) within a range, such as from 1 millimeters to 20 millimeters. The device 10 may be configured to have the opening diameter changed several times, such as going from an initial open configuration (and first diameter) and then further expanded (or contracted) to a second open configuration (and second diameter) and then to a $3^{rd}$, $4^{th}$, etc., configuration/diameter. As the access opening 27 goes from closed to one or more open configurations, the outer diameter of the main body 14 may also vary. For example, the main body may have an outer diameter of 3 to 4.5 millimeters when in the unexpanded configuration, and may have an outer diameter of around 15 millimeters, and/or in the range of 10 to 20 millimeters or even more, when in the expanded configuration(s).

In one example of use of a device 10 according to the invention for a transapical heart valve replacement, a prosthetic heart valve may be mounted on a prosthetic heart valve delivery catheter having an outer diameter of 18 to 24 French (i.e., 6 mm to 8 mm) It may be desirable for a delivery sheath to first be introduced through the device 10, with the prosthetic heart valve delivery catheter then being advanced through the delivery sheath. Such a delivery sheath might have an outer diameter of 6 to 12 millimeters, depending on the particular application. For example, sheaths having outer diameters of 8 to 10 millimeters (and more specifically of 8.5 millimeters and 9.3 millimeters) are known for use in delivering Edwards "Sapien" prosthetic heart valves via a transapical approach. Such a delivery sheath could be advanced through the device 10, with the device 10 expanding so that the opening 27 forms its shape and enlarges its dimensions to accommodate the delivery sheath therethrough.

When the main body 14 is in its radially unexpanded configuration, the sealing fabric 46 may largely or completely fill and seal the inner lumen 24, thereby substantially or completely closing off the opening 27, as depicted in FIGS. 3A-3D. The main body 14 in its unexpanded configuration may exert a defined force radially inward against the sealing fabric or other portion of the hemostatic seal 44, which can assist the hemostatic seal 44 in sealing the device 10.

The sealing fabric 46 may have a proximal portion 48 extending over and out of the main body 14 by some distance, such as 5 mm to 20 mm, on the proximal end 16 of the main body 14 to facilitate suturing, or attachment by other suitable means, of the device 10 to the myocardium or other target tissue.

Figure 5A:
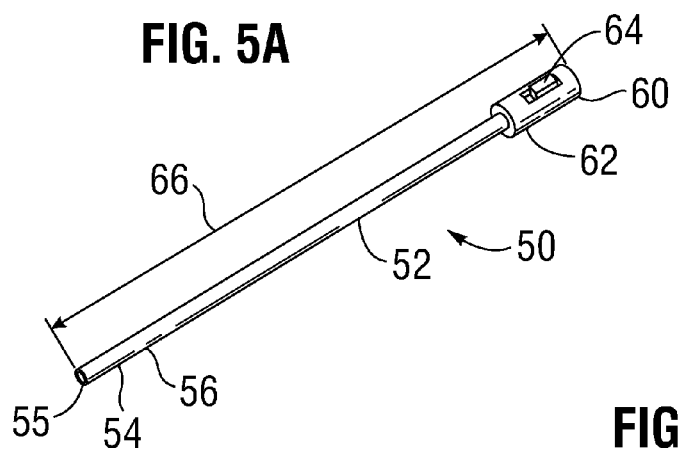
FIGS. 5A-5B are perspective and side (cross-sectional, close-up) views of an example of a delivery system according to an embodiment of the current invention.
Figure 5B:
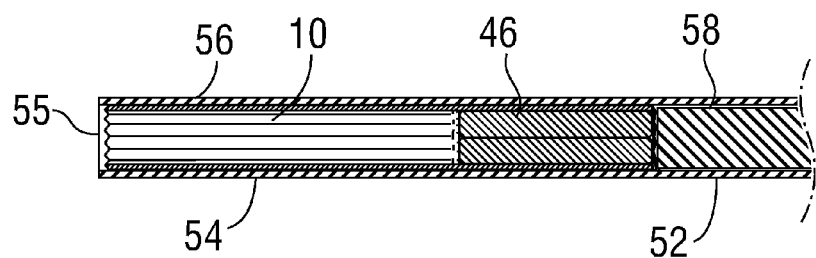

FIGS. 5A-5B depict a delivery system 50 according to an embodiment of the invention. The delivery system 50 includes a delivery catheter 52 having a distal portion 54 with a distal opening 55. A hemostatic access port device 10 is positioned within the distal portion 54. The delivery catheter 52 has an outer sheath 56 with an inner rod 58 slidingly disposed therein. The device 10 is positioned within the outer sheath 56 at a position just distal of the inner rod 58. The delivery catheter 52 includes a proximal end 60 having a handle 62 with one or more controls 64 for advancing and/or retracting the inner rod 58 with respect to the outer sheath 56 (or for retracting the sheath 56 with respect to the inner rod 58). The delivery catheter 52 may have a length 66 sufficient for a user to hold the handle 62 at a position outside of the patient while the distal portion 54 is positioned at a desired position within the patient (e.g., adjacent or within the heart wall).

Figure 6A:
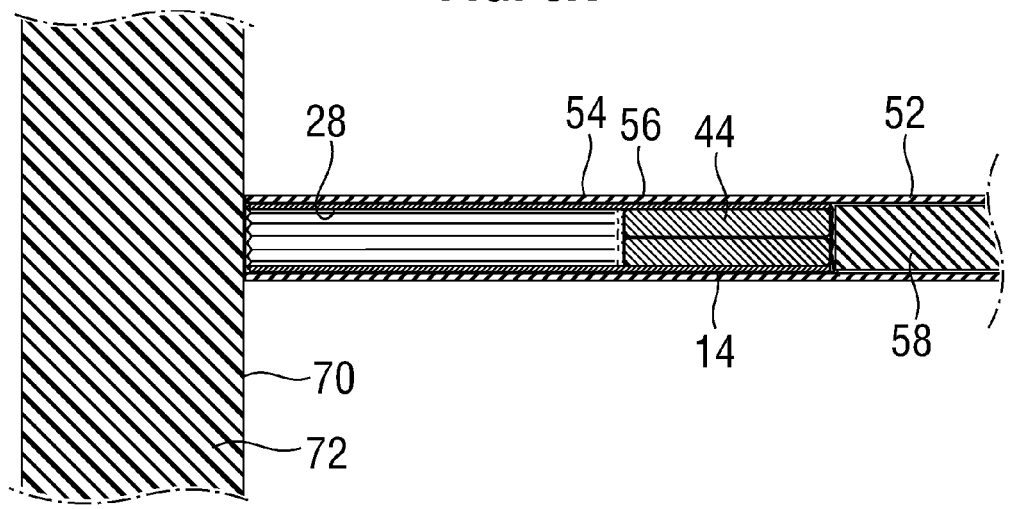
FIGS. 6A-6E are side views of a device being deployed in a heart wall according to an embodiment of the invention.
Figure 6B:
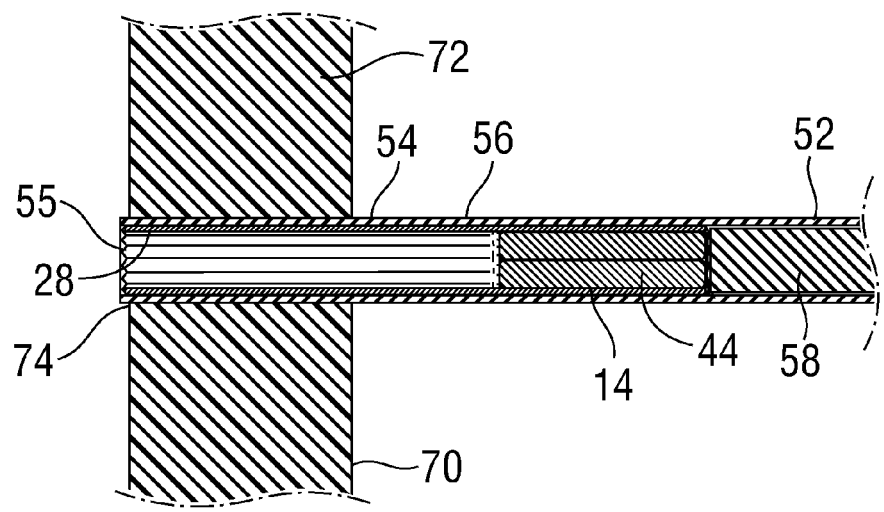

FIGS. 6A-6E depict deployment of a device 10 into the wall of a body organ according to an embodiment of the invention. In FIG. 6A, the distal portion 54 of the delivery catheter 52 is positioned against an outer surface of a body organ wall, which in the particular embodiment depicted is the outer surface 70 of the heart wall 72. The device 10 is positioned, in its delivery configuration, within the distal portion 54. In FIG. 6B, the distal portion 54 of the delivery catheter 52 is advanced into and through the heart wall 72 via an opening 74 therein. Note that the opening 74 may have been previously formed via a separate tool, such as a trocar, or may be formed by the delivery system itself, such as where the delivery catheter includes a puncture device at its distal end.

Figure 6C:
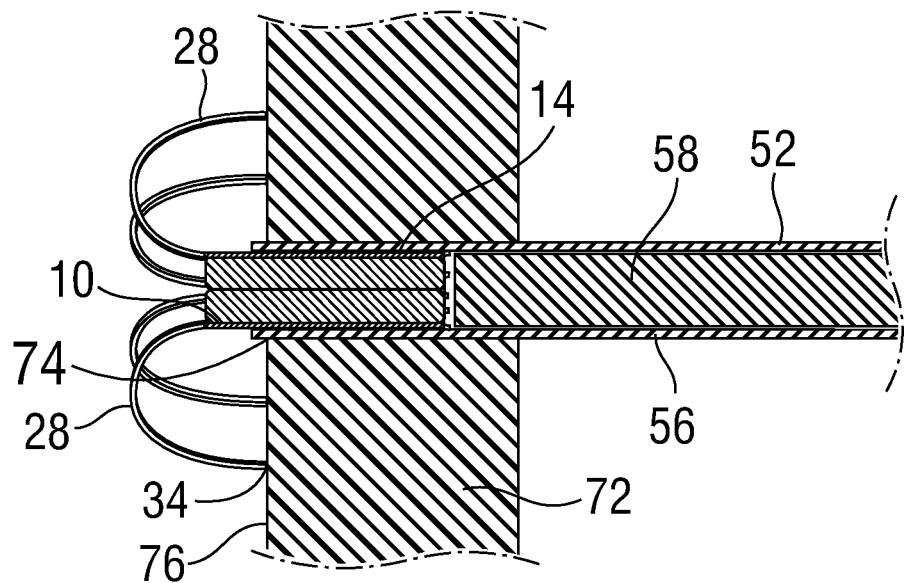

As depicted in FIG. 6C, the device 10 is slidingly advanced partially out of the delivery catheter 52, such as by being pushed out of the outer sheath 56 by advancement of the inner rod 58. As the device 10 is advanced out of the sheath 56, the prongs 28 assume their curved configuration, with their distal ends 34 arcing backwards and engaging into the heart wall 70 from an interior surface 76 thereof.

Figure 6D:
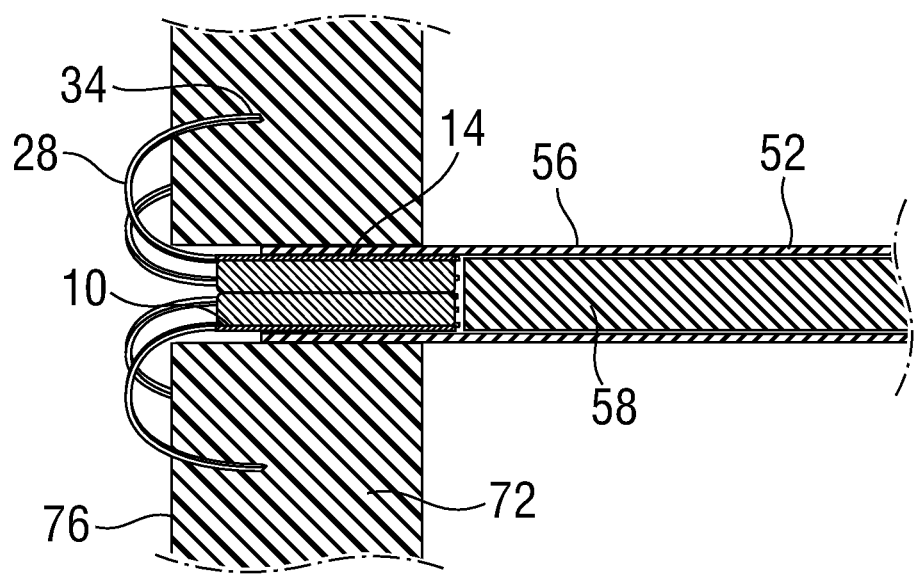

FIG. 6D depicts the delivery catheter 52 being partially withdrawn. The device 10 is pulled partially backward (proximally) to cause the distal ends 34 of the prongs 28 to be driven into and embedded within the inner surface 76 of the heart wall 72. In an embodiment of the delivery catheter where a device fits relatively tightly within the outer sheath, the inward pressure of the outer sheath against the device provides a frictional engagement that pulls the device proximally as the sheath is withdrawn proximally from the heart wall.

Figure 6E:
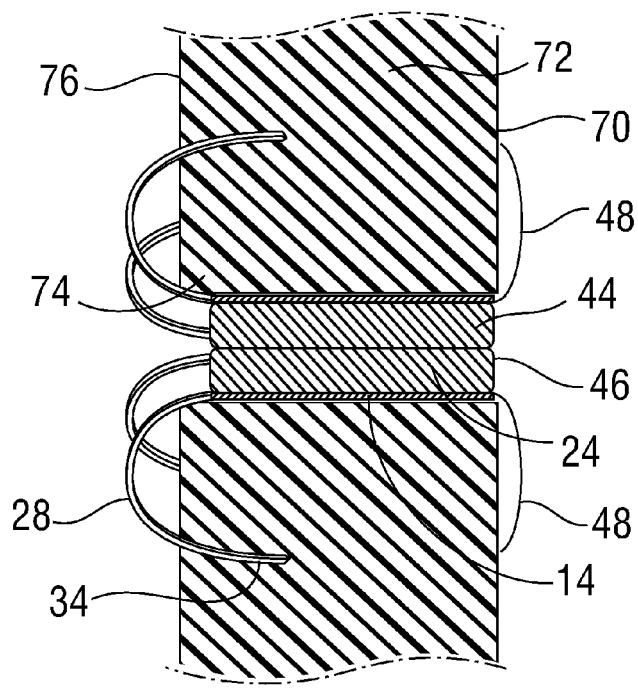

With the delivery catheter removed entirely from the heart wall 72, as depicted in FIG. 6E, the device 10 is fully deployed and assumes its closed configuration, with the prongs 28 in their curved configuration and embedded in the heart wall 72 through the inner surface thereof, and with the main body 14 passing through the heart wall 72 and in the unexpanded configuration. The sealing fabric 46 extends through the main body inner lumen 24 to provide a hemostatic seal 44 therein. The proximal portion 48 of sealing fabric 46 extends across a portion of the outer surface 70 of the heart wall 72. The proximal portion 48 of sealing fabric 46 may be sutured or otherwise secured to the outer surface 70 of the heart wall 72.

Figure 7A:
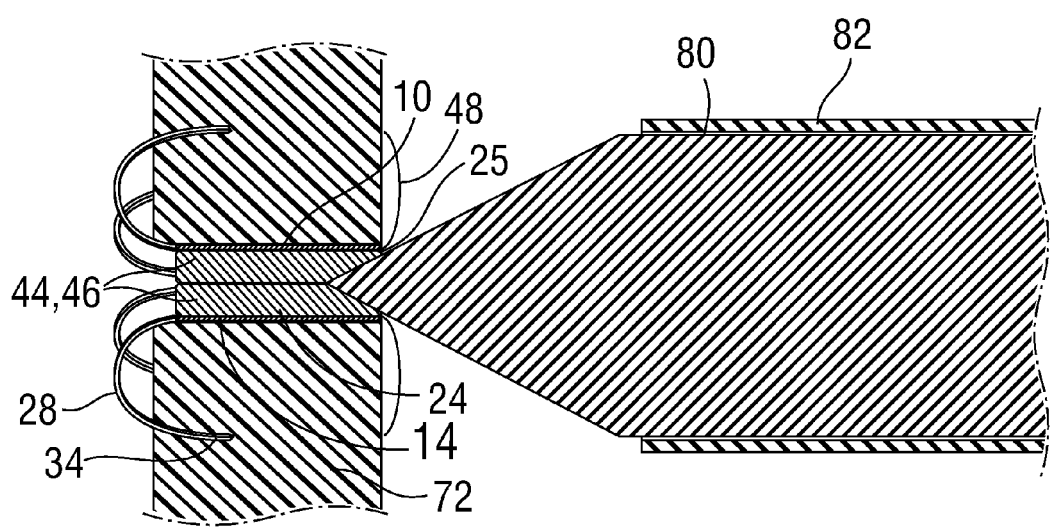

FIGS. 7A-7E depict a procedure wherein a dilator 80 and access sheath 82 are used to provide access to the heart interior via a device 10 according to an embodiment of the invention. As depicted in FIG. 7A, the dilator 80 with access sheath 82 is advanced into the proximal opening 25 of the inner lumen 24 of the device 10. As the dilator 80 and access sheath 82 are advanced into the device 10, the dilator 80 forces the main body 14 and hemostatic seal 44 to radially expand to assume the radially expanded and open configuration outward, thus creating the opening 27 through which the dilator 80 and access sheath 82 are advanced, as depicted in FIG. 7B.

With the device 10 expanded and with the access sheath 82 deployed therein, the dilator 80 is removed, as depicted in FIG. 7C. The access sheath 82 provides convenient access for performing one or more procedures on the interior of the heart, which may include the introduction and/or removal of surgical tools, implant devices, etc. to/from the heart interior through the heart wall 72.

Figure 7D:
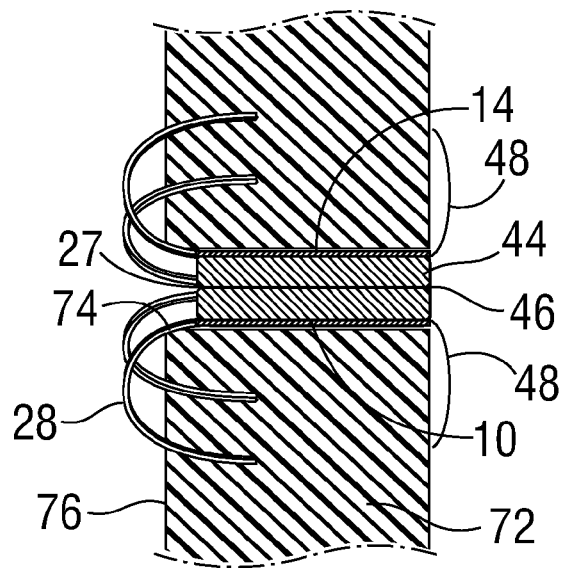
Figure 7E:
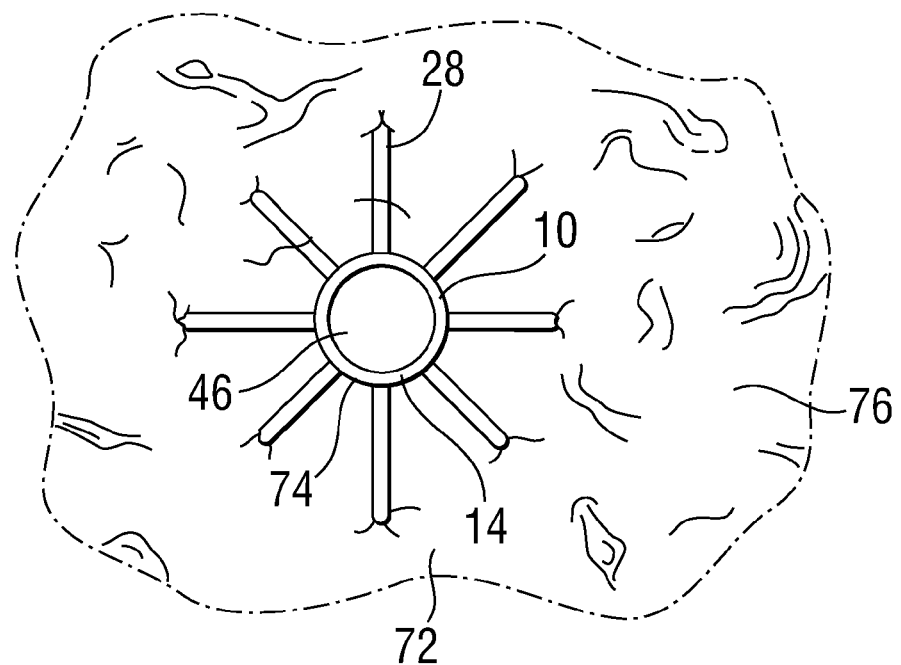
FIG. 7E depicts a distal end view of a device deployed in the heart wall according to an embodiment of the invention.
Figure 8:
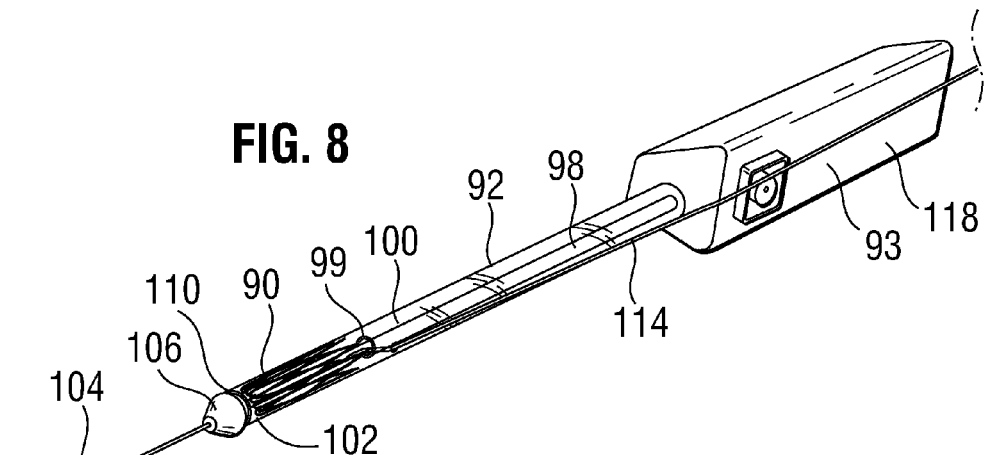
FIG. 8 is a perspective view of a delivery system according to an embodiment of the invention.

When the desired procedure(s) have been performed, the access sheath 82 can be withdrawn, as depicted in FIGS. 7D and 7E. The device 10 returns to its closed configuration, with the main body 14 returning to its unexpanded diameter and pressing inwardly against the sealing fabric 46 to form the hemostatic seal 44. The closed device 10 can thus be left in position in the heart wall 72, with the prongs 28 advanced into the heart wall 72 from the interior surface 76 thereof.

Note that other variations of the device are also within the scope of the invention. For example, the device may be fitted with additional structures for attaching the device to the tissue, such as prongs and/or barbs at the proximal end of the main body and/or in the midsection thereof. The hemostatic seal may be positioned at either end and/or in the middle of the main body. Sealing of the inner lumen may be augmented by inserting a suitable material into the lumen prior to contraction of the main body to its closed/unexpanded diameter. A fabric flap and/or valve-like structure may be attached to either end of the main body to assist in sealing the lumen.

In a further embodiment of the invention depicted in FIGS. 8 and 9A-9E, a device 90 is delivered via a catheter 92 configured to minimize the amount/length of catheter advanced into the heart or other organ. The device 90 is introduced such that its prongs 94 are already in their swept-back configuration with respect to the device main body 96 during introduction, such that there is no sweeping motion of the prongs 94 as they are released from the catheter 92. To achieve this deployment, the catheter 92 is a coaxial catheter having an inner sheath 98 and an outer sheath 100.

The device 90 is positioned within the catheter 92 at a distal end portion 102 thereof, as depicted in FIGS. 8 and 9A-9E. The catheter 92 has a handle 93 with one or more controls thereon. The inner sheath 98 is configured to track over a guidewire 104, and includes a tapered transition tip 106 which transitions from the inner sheath distal end 108 to the leading edge 110 of the outer sheath 100. There is sufficient clearance between the inner sheath 98 and outer sheath 100 for the device 90 to be positioned therebetween.

The device 90 is positioned on the inner sheath 98, just proximally of the transition tip 106, with the outer sheath 100 extending over the device 90 with its leading edge 110 adjacent the transition tip structure 106. The device 90 is thus restrained to a relatively small radial diameter 112a, but with its prongs 94 in a swept-back position, by the outer sheath 100. The main body 96 of the device 90 is positioned about inner sheath 98, and may press radially inwardly against the inner sheath 98 to assist in holding the device 90 at the desired position on the inner sheath 98. The inner sheath 98 may have a step 99 positioned just proximally of the device 90 which prevents the device from sliding proximally along the inner sheath 98.

A suture thread 114 passes through the main body 96 of the device 90 (or is otherwise secured to the device) and out of the catheter 92 via a suture hole 116 in the outer sheath 100. The suture thread 114 passes proximally along the catheter 92 to the proximal end portion 118 and handle 93 thereof. The suture thread 114, or a similar structure capable of creating a proximal pulling force on the device 90, can assist in device deployment, as discussed later in this application. The suture thread 114 pass from a proximal portion of the catheter, up and through a portion of the device, and then back to the proximal portion of the catheter, thereby forming a double line of suture.

Figure 9A:
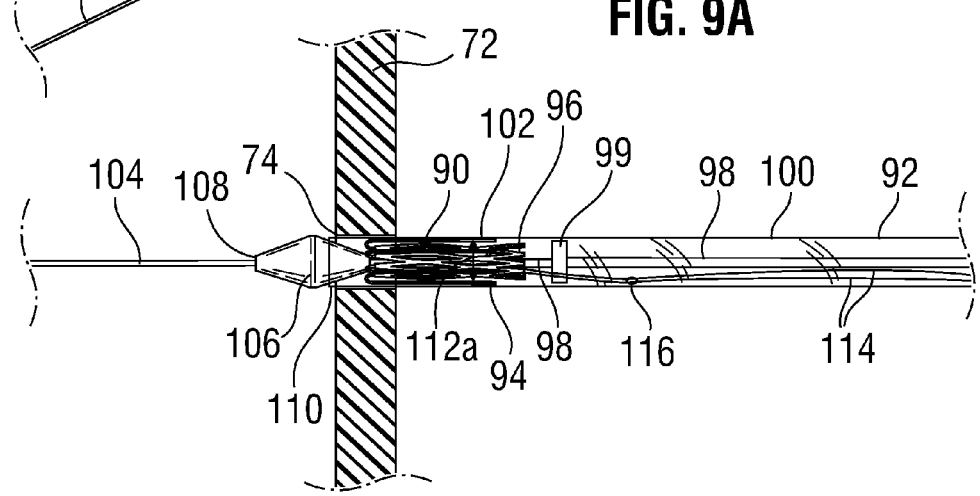
FIGS. 9A-9E are side views of the delivery system of FIG. 8 deploying a device into the heart wall.

Note that with the device 90 folded or otherwise positioned in the catheter between the inner sheath 98 and outer sheath 100, the prongs 94 of the device 90 are folded down to approximately the delivery diameter 120a of the main body 96, thereby minimizing the profile of the device 90. As depicted in FIG. 9A, the catheter 92 and device 90 can be advanced into the heart into an interior portion thereof (such as a ventricle) through an opening 74 in the heart wall 72.

Figure 9B:
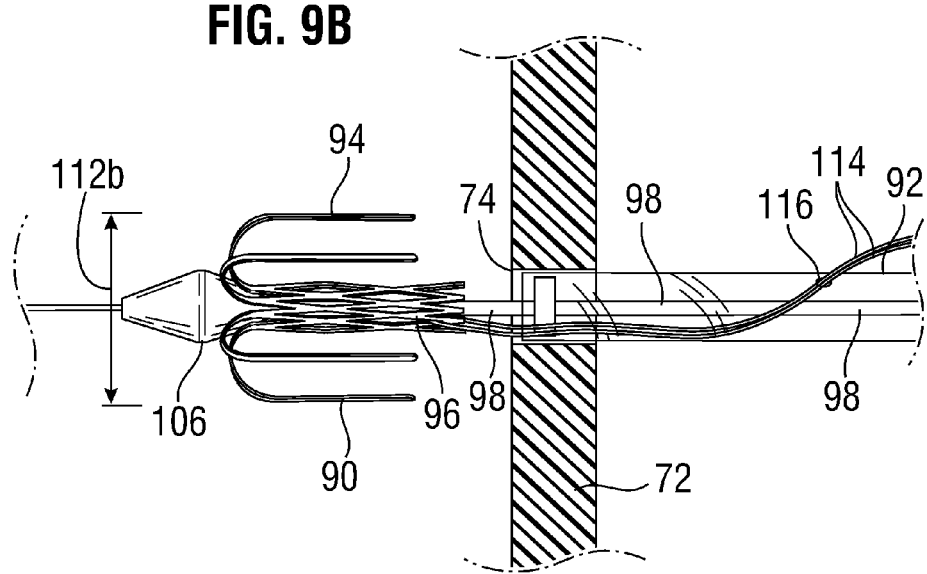

With the device 90 advanced through the heart wall 72, the outer sheath 100 is retracted proximally with respect to the inner sheath 96 and device 90, as depicted in FIG. 9B. As the outer sheath 100 slides off of the device 90, the prongs 94 spring radially outward to a larger diameter 112b. The larger diameter 112b is larger than the diameter of the opening 74 in the heart wall 72.

Figure 9C:
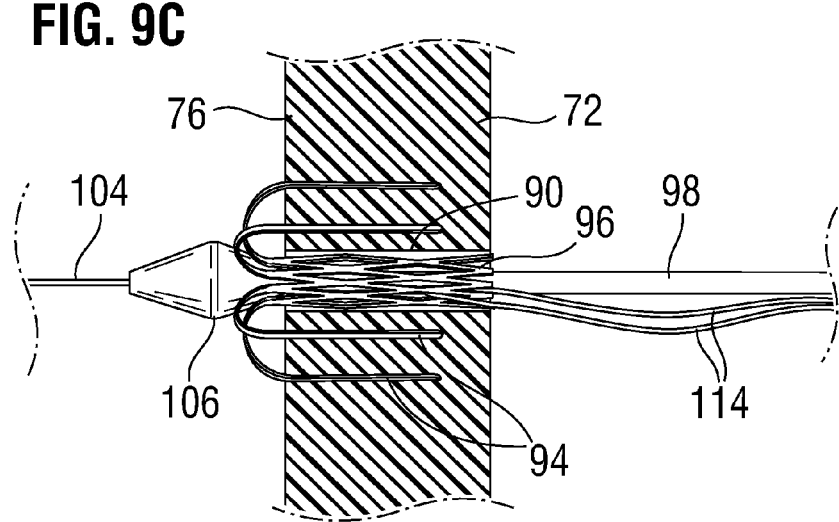

The device 90 is retracted proximally into the interior surface 76 of the heart wall 72 to embed the prongs 94 into the heart wall 72, as depicted in FIG. 9C. Proximal retraction is achieved by pulling the inner sheath 98 proximally with the device 90 thereon, and/or by pulling proximally on the suture thread 114, to thereby press the prongs 94 into the heart wall 72. Note that a proximal portion of the suture thread may be secured to a proximal portion of the inner sheath and/or other proximal portion of the catheter, so that proximal movement of the inner sheath results in corresponding proximal movement of the suture, so that the device is pulled proximally as the inner sheath is retracted.

Figure 9D:
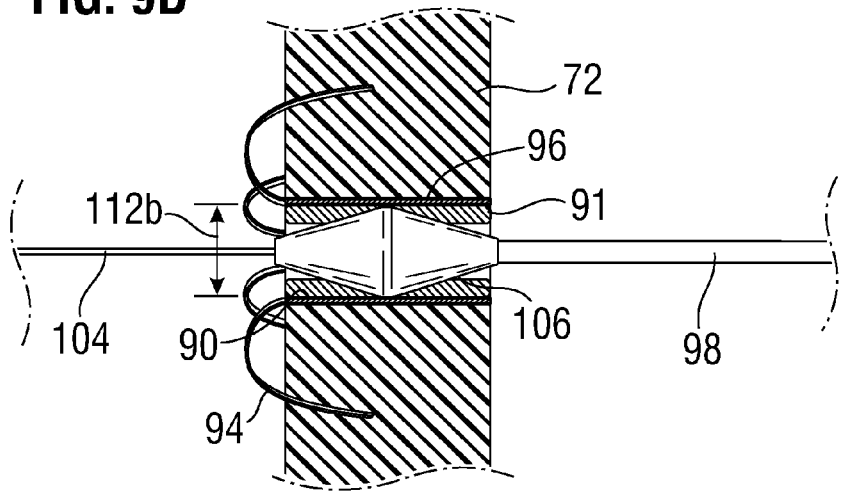

With the device 90 embedded in the heart wall 72, the one end of the suture thread 114 can be pulled while the other end is released, thus permitting the suture thread 114 to be pulled out of the device 90. The inner sheath 98 can be withdrawn through the device 90, as depicted in FIG. 9D. As the tapered transition tip 106 (which may be tapered at either or both its proximal and distal ends) is withdrawn, its tapered proximal portion thereof dilates the device main body 96 to an enlarged diameter 112b, and also compresses the sealing material 91 radially outward, thereby providing sufficient room for the inner sheath 98 and tapered transition tip 106 structures to be withdrawn entirely from the heart and device 90.

Figure 9E:
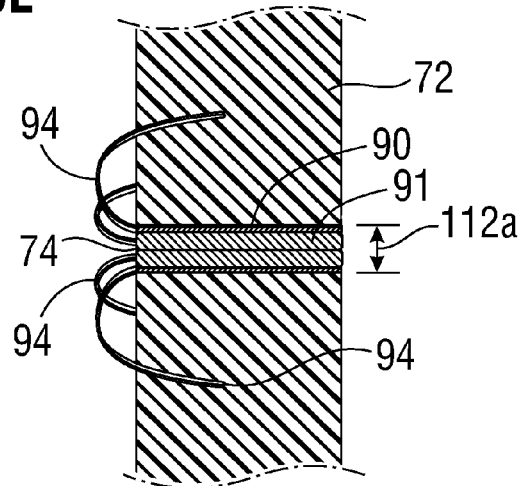
Figure 10A:
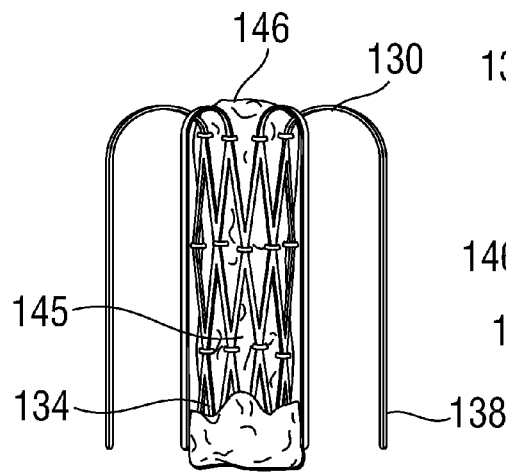
FIGS. 10A-10D are side, side (cross-sectional), distal, and proximal views of a device according to an embodiment of the invention.
Figure 10B:
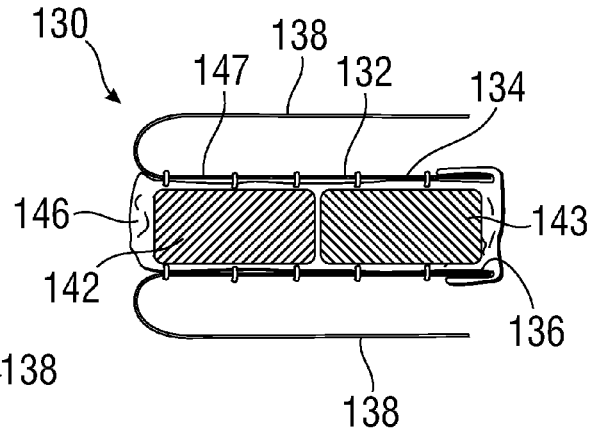
Figure 10C:
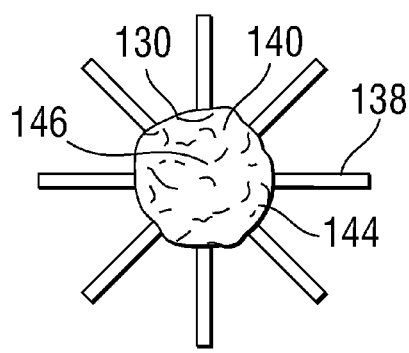
Figure 10D:
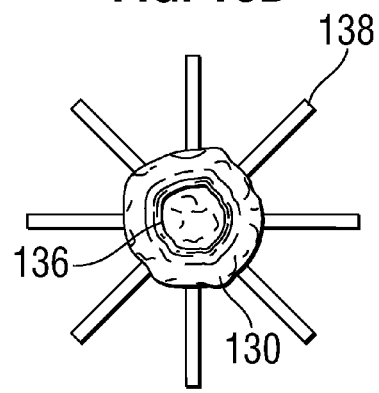

FIG. 9E depicts the device 90 fully deployed in the heart wall 72. The main body 96 has returned to its smaller diameter 112a, and the device 90 (e.g., using internal sealing material 91) provides a hemostatic seal at the opening 74 in the heart wall 72. With the device 90 thus deployed, a user can advance various dilators, sheaths, and/or other desired devices into the heart 70 through the device 90, using, e.g., the methods discussed elsewhere in this application (including those depicted in FIGS. 6A-6E).

FIGS. 10A-10D depict a device 130 according to a further embodiment of the invention. The device 130 includes a support structure 132 comprising a main body 134, inner lumen 136, and prongs 138 similar to those disclosed elsewhere in this application. A hemostatic seal 140 may include a foam-like material 142 and/or hydrogel component 143, which in the embodiment depicted is wrapped with a tightly woven or knit fabric 144. The foam 142 and/or hydrogel component provide bulk to contour to the lumen 136 of the support structure 132, while also allowing compressibility to allow passage of dilators and other devices through the lumen 136. When in its normal (relaxed) state, the foam 142 and/or hydrogel component 143 fill the lumen 136, and the fabric 144 wrapping the foam 142 and/or hydrogel component 143 provides a surface 146 generally across/perpendicular to the lumen 136 (and facing into the heart interior when deployed in the heart wall) for blood to coagulate and heal the wound/opening in the heart wall. By providing the surface perpendicular to the support structure 132 (and therefore generally parallel to the interior surface of the heart wall), the sealing fabric 144 minimizes the amount of clotting and scarring formed. To prevent blood from leaking through the sides of the lumen 136 of the support structure 132, additional sealing fabric 145 may cover the circumference of the lumen 136.

The device is preferably made from biocompatible materials. All or portions of the device may be bioabsorbable, bioerodible, biodegradable, and/or configured to encourage tissue ingrowth. Some portions may be configured to resist bioabsorption/biodegradation and/or to resist tissue ingrowth.

Examples of support stent materials for use with the invention include biocompatible materials such as stainless steel, nitinol, tantalum, titanium, cobalt-chromium, gold, silver, and polymers. Examples of hydrogels which can be used with the invention include biocompatible hydrogels such as crosslinked gelatin, polyhydroxyethyl methacrylate, polyethylene glycol (PEG), polyurethane (PU), and polyvinyl alcohol (PVA) hydrogels. Examples of foams for use with the invention include biocompatible foams such as PU foam. Examples of fabrics (for fabric wrappings, linings, etc.) for use with the invention include biocompatible fabrics such as PET and PTFE.

The device may comprise materials to enhance visibility with various medical imaging techniques, such as fluoroscopy, ultrasound, magnetic resonance, etc. For example, the device may include gold markers on the stent to enhance visibility of the device using fluoroscopy.

Figure 11:
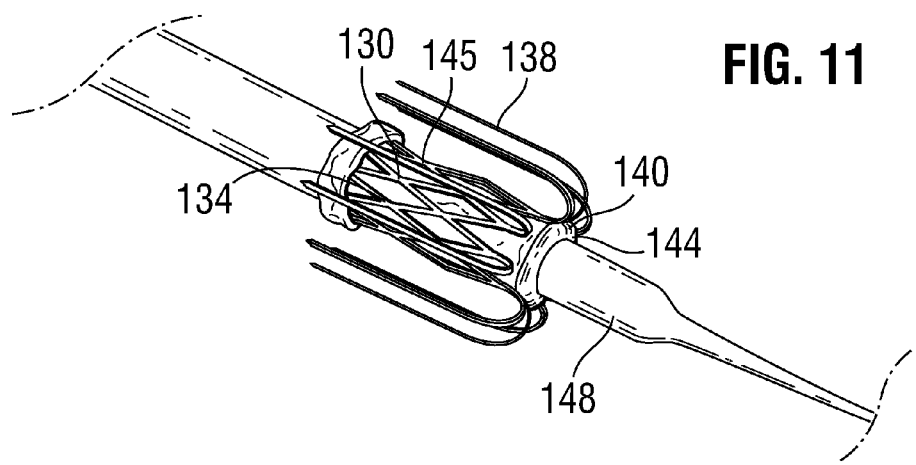
FIG. 11 is a perspective view of the device of FIGS. 10A-10D with a dilator advanced therethrough.

In one embodiment of the invention, such as that depicted in FIG. 11, the sealing fabric 144/foam 142/hydrogel 143 assembly is attached within the lumen 136 (e.g., via sutures) at only one side 147 thereof so that a dilator 148 or other device can be introduced into and through the device 130 to thereby open the lumen 136 to a larger diameter for access into the heart. When the dilator 148 enters the lumen 136, it compresses the fabric-wrapped foam 142 and/or hydrogel 143 up against the one side 147 of the lumen 136, so that when the lumen 136 is expanded by the dilator 148 the fabric-wrapped foam 142 does not interfere with access through the lumen 136. Although in FIG. 11 only a dilator is shown, in a typical application the dilator would include a guide catheter and/or sheath, where upon removal of the dilator the guide catheter and/or sheath would remain in place within the device to provide access through the catheter/sheath into the heart.

Figure 12:
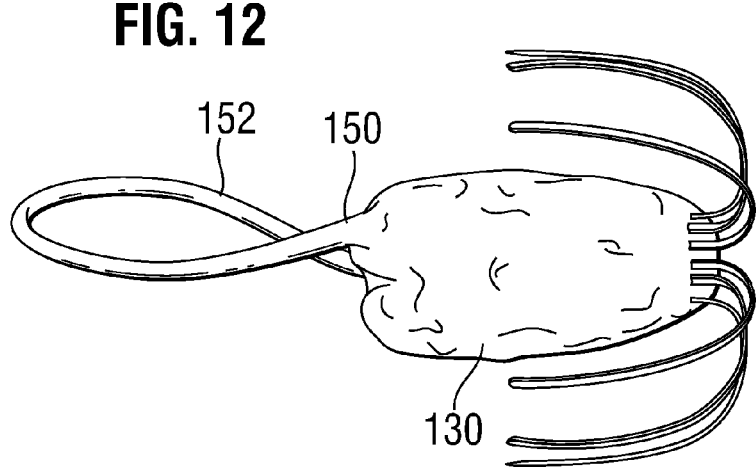
FIG. 12 is a side view of a hemostatic device according to an embodiment of the invention.
Figure 13A:
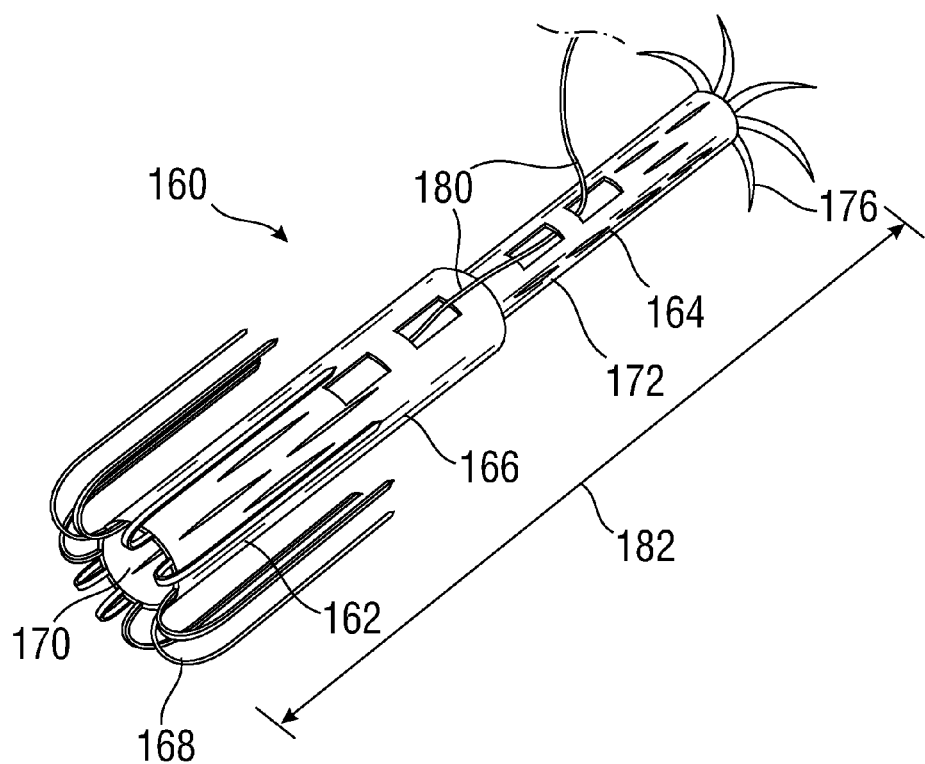
FIG. 13A is a perspective view of a hemostatic device according to an embodiment of the invention.
Figure 13B:
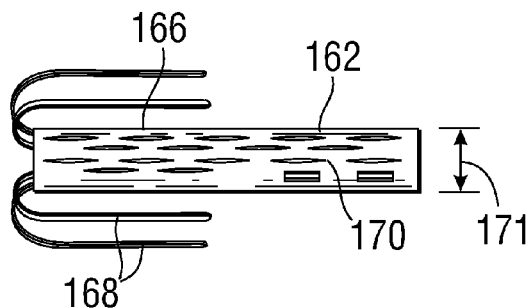
FIG. 13B is a side view of a distal portion of the hemostatic device of FIG. 13A.
Figure 13C:
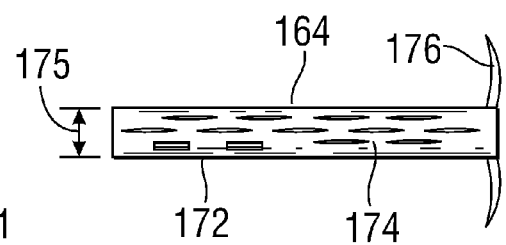
FIG. 13C is a side view of a proximal portion of the hemostatic device of FIG. 13A.
Figure 13D:
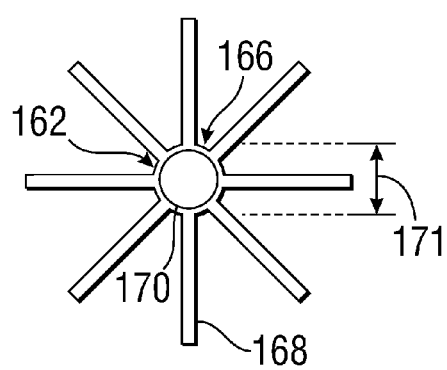
FIG. 13D is a distal end view of a distal portion of the hemostatic device of FIG. 13A.
Figure 13E:
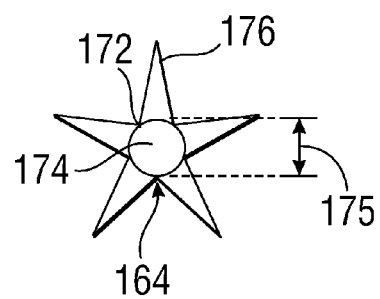
FIG. 13E is a proximal end view of a proximal portion of the hemostatic device of FIG. 13A.

In a further embodiment of the invention, additional sealing fabric 150 is provided which is tailored to be sutured or otherwise secured to a position outside of the heart, thus providing a resistant force preventing the device 130 being pushed distally into the heart upon interaction with instruments, such as with the dilator used to open the device 130. The additional sealing fabric 150 may include an extension 152 such as that depicted in FIG. 12, which the surgeon or other user would grasp and hold (for example, with a clamp) to provide a resisting force against distal displacement of the device 130. Note that the extension can be configured in many ways, and that the configuration depicted in FIG. 12 is only one example of such an extension.

FIGS. 13A-13E depict a further embodiment of methods and structures for access and stabilization (e.g., to prevent a device according to the invention from being pushed distally into the heart after deployment), and/or to accommodate heart walls of varying thicknesses. The device 160 includes a distal portion 162 and a proximal portion 164. The distal portion 162 includes a distal main body 166 and distal prongs 168, with a distal lumen 170 and distal outer diameter 171. The proximal portion 164 includes a proximal main body 172, proximal lumen 174, proximal flared extensions 176, and proximal outer diameter 175.

The distal lumen 170 of the distal portion 162 is sized to receive the proximal main body 172 of the proximal portion 164, thereby creating a single device 160 having a continuous lumen 178 therethrough. The distal portion 162 and proximal portion 164 may be removably or permanently secured to each other via suture 180 or other mechanical means, which may also be used to adjust or otherwise vary the overall length 182 of the device 160.

The proximal portion 164 may be configured to slide within the distal lumen 170, thus permitting the overall length 182 of the device 160 to be varied according to the particular application (e.g., to accommodate thicker or thinner heart walls, etc.). Hemostatic seals (not depicted) such as those discussed and depicted previously, e.g., in FIGS. 10A-10D and 11 may be included in one or both of the distal lumen 170 or the proximal lumen 174.

Figure 14A:
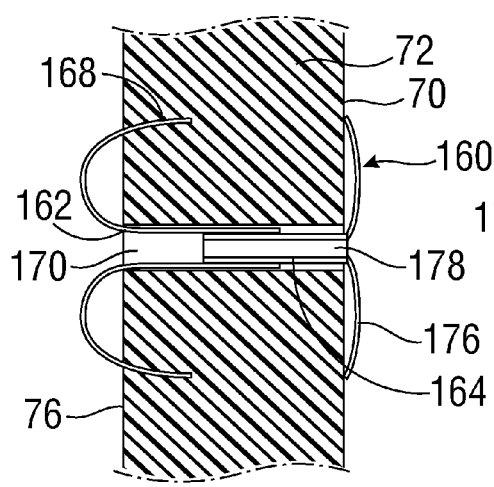
FIG. 14A is a side view of a hemostatic device deployed in the heart wall according to an embodiment of the invention.

As depicted in FIG. 14A, in one embodiment the device 160 is configured to provide access and a hemostatis by having the distal portion 162 positioned in the heart wall 72 adjacent an inner surface 76 thereof, and with the proximal portion 164 positioned in the heart wall 72 adjacent an outer surface 70 thereof. In such an embodiment, the device 160 provides a continuous lumen 178 extending from the outside surface 70 to the inside surface 76 of the heart wall 72

Figure 14B:
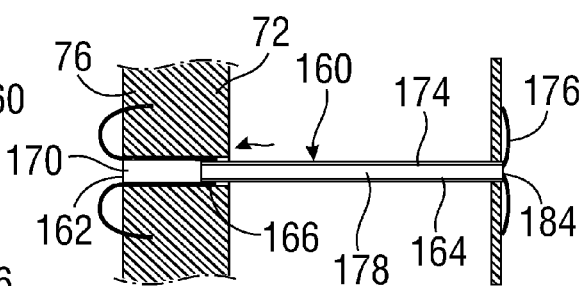
FIG. 14B is a side view of a hemostatic device deployed in the heart wall and entry point incision according to an embodiment of the invention.

In a further embodiment, depicted in FIG. 14B, a device 160 is configured to have the distal portion 162 positioned in the heart wall 72 adjacent an inner surface 76 thereof, but with the proximal portion 164 positioned in the incision site 184 in the patient's skin through which the procedure is being conducted. In such an embodiment, the proximal portion 164 has sufficient length to reach from the incision site 184 and into the heart wall 72 and distal lumen 170 of the distal portion 162. The overall length of the device 160, which may be adjustable by sliding the distal and proximal portions with respect to each other, thus reaches from the incision site 184 and into the heart wall 72, thereby providing a continuous lumen 178 through which the heart may be accessed from outside of the patient.

The distal portion 162 may be configured to remain in the heart at the conclusion of the procedure and provide an appropriate seal for the opening 74 in the heart wall 72. The proximal portion 164 may be configured to remain in the heart and/or incision site, and/or may be configured to be removed entirely from the patient at the conclusion of the particular procedure.

Note that any of the delivery/deployment systems and methods depicted herein could be used with any of the devices described herein. For example, the delivery/deployment system and methods depicted in FIGS. 5A-5B and 6A-6E could be used with the device depicted in FIGS. 1A-3C as well as the device depicted in FIGS. 10A-10D, 12, and 13A-13E. The delivery/deployment system and methods depicted FIGS. 8 and 9A-9E could be used with the device depicted in FIGS. 1A-3C as well as the device depicted in FIGS. 10A-10D, 12, and 13A-13E. The deployment methods depicted in FIGS. 14A-14B could be used with the devices depicted in FIGS. 1A-1C, 10A-10D, 12, and 13A-13E, and also with the delivery/deployment systems of FIGS. 5A-5B, 6A-6E, 8, and 9A-9E.

One surgical procedure that may utilize the devices of the present application is a transapical heart valve replacement through the left ventricular apex, as disclosed in U.S. Patent Publication No. 2007-0112422 to Dehdashtian, filed Nov. 16, 2005, and in U.S. Provisional Application No. 61/220,968 to Pintor, filed Jun. 26, 2009, the disclosures of which are expressly incorporated herein by reference. First, the prosthetic heart valve and various delivery instruments are selected and prepared for use by removing them from any packaging and rinsing or sterilizing as needed. The prosthetic heart valve is then crimped over the balloon on the catheter.

Next, a puncture is formed in the heart wall, which in one embodiment is formed at the apex of the left ventricle. A guidewire is advanced into the heart via the puncture. Next, the surgeon advances a delivery catheter having a hemostatic device according to the invention, with the delivery catheter and hemostatic device advanced over the guidewire. Note that the delivery catheter may itself form the initial puncture, in which case the guidewire may be advanced out of the delivery catheter and into the heart after the delivery catheter creates the puncture through the heart wall. The guidewire is passed through the native valve (e.g., the aortic valve) and into the areas above the native valve (e.g., the ascending aorta (AA)). A pre-dilation step of the valve annulus may be performed to enlarge or crack existing calcification in the annulus. The surgeon then inserts a dilator and introducer sheath into the ventricle through the apical puncture, using the hemostatic device as an access port.

The balloon catheter (or other appropriate valve delivery system) is advanced over the guidewire and through the introducer sheath. The surgeon locates the prosthetic heart valve at the annulus and between the native valve leaflets. Radiopaque markers may be provided on the distal tip of the introducer sheath to more accurately determine its position relative to the valve and balloon. When the surgeon is satisfied of the proper positioning and rotational orientation of the valve, the valve is expanded into contact with the annulus. For example, for a balloon-expanded prosthetic valve, the balloon is expanded into contact with the annulus, thereby expanding the prosthetic valve. If the prosthetic valve is self-expanding, the prosthetic valve is released from its constraints (e.g., an outer sheath) to expand into contact with the annulus.

The surgeon then deflates the balloon (if applicable) and withdraws the entire delivery system over the guidewire. The introducer sheath is withdrawn, followed by (or preceded by) the guidewire. Ultimately, the hemostatic device is collapsed to its unexpanded diameter, as previously described herein, thus sealing the puncture.

The exemplary procedure may be performed as a first time valve implant or to supplement a previous implant. A relatively large proportion of recipients of prosthetic heart valves are older, typically older than 60. Over time, prosthetic heart valves have been known to show reduced performance and even failure. Re-operating on septuagenarians and even octogenarians is problematic. However, a port access procedure such as disclosed herein eliminates open-heart surgery and potentially cardiopulmonary bypass, and is therefore more desirable for the aging patient. Therefore, the present invention contemplates transapical implantation of a prosthetic heart valve over an existing prosthetic valve implant. In such a case, a pre-dilation step is typically not necessary, though it is conceivable.

The prosthetic heart valve implantation procedure described herein may be performed in conjunction with cardiopulmonary bypass, or without bypass in a so-called off-pump procedure. The necessity for bypass depends on a number of factors, including the patient's age, vulnerability to such a procedure, and viability of the native leaflets. Ideally, the implantation procedure is performed off-pump.

While the invention has been described in various embodiments, it is to be understood that the words which have been used are words of description and not of limitation. Therefore, changes may be made within the appended claims without departing from the true scope of the invention.

What is claimed is:

1. A device for providing access through and sealing of a puncture in tissue, comprising:
a generally elongated and radially-expandable main body, the main body comprising a distal portion having a distal end and a distal lumen and a proximal portion having a proximal end and a proximal lumen, the distal lumen being sized to receive the proximal lumen, thereby creating a continuous internal lumen through the main body, the main body having an unexpanded configuration having an unexpanded outer diameter, the main body further having an expanded configuration having an expanded outer diameter;
a plurality of prongs extending from the distal end of the distal portion of the main body, each of the prongs comprising a proximal end secured to the distal end of the distal portion of the main body, each of the prongs further comprising a distal end, wherein each of the prongs comprises a straight configuration wherein the prong is generally straight and extends generally distally from the main body distal portion such that the distal end of the prong is positioned distally of the main body, each of the prongs further comprising a bent configuration wherein the prong is generally curved such that the distal end of the prong is positioned radially outward from the main body and the distal end of the prong is positioned proximally of the distal portion of the main body;
wherein the device comprises a delivery configuration, an access configuration, and a closed configuration, and further wherein in the delivery configuration the main body is in the unexpanded configuration and the prongs are in the straight configuration; wherein in the access configuration the main body is in the expanded configuration and the prongs are in the curved configuration; and wherein in the closed configuration the main body is in the unexpanded configuration and the prongs are in the curved configuration; wherein a hemostatic barrier positioned within the distal lumen, the proximal lumen, or both, and configured to prevent fluid leakage proximally and distally through the inner lumen when the main body is in the unexpanded configuration.

2. The device of claim 1, wherein the main body comprises a memory material having a relaxed state, and wherein the main body is biased, when in the relaxed state, toward the unexpanded configuration.

3. The device of claim 1, wherein the prongs comprise a memory material having a relaxed state, and wherein the prongs are biased, when in the relaxed state, toward the curved configuration.

4. The device of claim 3, wherein the main body comprises the memory material, and wherein the main body is biased, when in the relaxed state, toward the unexpanded configuration, such that the device is biased toward the closed configuration.

5. The device of claim 4, wherein the prongs and main body comprise Nitinol.

6. The device of claim 1, wherein the prongs and main body comprise a unitary structure.

7. The device of claim 1, wherein the main body has an unexpanded external diameter when the main body is in the unexpanded configuration, and wherein the main body has an expanded external diameter when the main body is in the expanded configuration, wherein the unexpanded external diameter is less than the expanded external diameter.

8. The device of claim 7, wherein the expanded external diameter is in the range of 10 to 20 millimeters.

9. The device of claim 7, wherein the unexpanded external diameter is in the range of 3 to 5 millimeters.

10. The device of claim 1, wherein the hemostatic barrier comprises a sealing fabric, wherein the sealing fabric covers the internal walls of the inner lumen of the main body.

11. The device of claim 10, wherein the main body in its unexpanded configuration exerts a radially inward force against the sealing fabric.

12. The device of claim 1, wherein a portion of the sealing fabric extends proximally past the proximal end of the proximal portion of the main body by a distance of 5 mm or more to facilitate suturing of the sealing fabric to tissue of the patient.

* * * * *